US008094874B2

(12) United States Patent
Dugan et al.

(10) Patent No.: US 8,094,874 B2
(45) Date of Patent: *Jan. 10, 2012

(54) MATERIAL CONTEXT ANALYSIS

(75) Inventors: Peter Dugan, Ithaca, NY (US); Robert L. Finch, Endicott, NY (US); Rosemary D. Paradis, Vestal, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 819 days.

This patent is subject to a terminal disclaimer.

(21) Appl. No.: 12/129,383

(22) Filed: May 29, 2008

(65) Prior Publication Data
US 2009/0052732 A1 Feb. 26, 2009

Related U.S. Application Data

(60) Provisional application No. 60/940,632, filed on May 29, 2007.

(51) Int. Cl.
  *G06K 9/62* (2006.01)
  *G01N 23/04* (2006.01)
  *G06K 9/00* (2006.01)
(52) U.S. Cl. ......................... 382/100; 378/57
(58) Field of Classification Search .......... 382/131–132, 382/141, 159, 164, 173, 181, 190, 199, 203, 382/209, 217, 224; 378/5, 9, 10, 24, 53, 378/55, 57, 88, 90, 119, 143, 145, 199; 706/47, 706/52; 315/500, 505; 430/572.1, 572.4; 340/568.1; 705/13
See application file for complete search history.

(56) References Cited

U.S. PATENT DOCUMENTS

| 5,319,547 A | 6/1994 | Krug et al. |
| 5,490,218 A | 2/1996 | Krug et al. |
| 5,600,303 A | 2/1997 | Husseiny et al. |
| 5,600,700 A | 2/1997 | Krug et al. |
| 5,642,393 A | 6/1997 | Krug et al. |
| 5,838,758 A | 11/1998 | Krug et al. |
| 6,018,562 A | 1/2000 | Willson |
| 6,026,171 A | 2/2000 | Hiraoglu et al. |
| 6,236,709 B1 | 5/2001 | Perry et al. |

(Continued)

OTHER PUBLICATIONS

Cajipe, V.B.; Calderwood, R.F.; Clajus, M.; Hayakawa, S.; Jayaraman, R.; Tumer, T.O.; Grattan, B.; Yossifor, O.; "Multi-Energy X-ray Imaging with Linear CZT Pixel Arrays and Integrated Electronics"; Date: Oct. 16-22, 2004; Source: Nuclear Science Symposium Conference Record, 2004 IEEE vol. 7, pp. 4548-4551 vol. 7.

(Continued)

*Primary Examiner* — Amir Alavi
(74) *Attorney, Agent, or Firm* — Miles & Stockbridge P.C.

(57) ABSTRACT

A process for contextual analysis of radiographic image data can be embodied as a method, system, and computer software program, among other things. The process can include receiving a radiographic image and performing a region analysis including identifying a region within the radiographic images having an estimated atomic number within a predetermined range and determining if the region is in an expected location. The process can also include performing a material feature analysis to identify whether a feature present in the radiographic image is associated with an obscuration characteristic. The process can include providing context information and generating, as output, a region of interest in the radiographic image, the region of interest being determined based upon a set of rules and the region analysis, the material feature analysis, and the context information.

20 Claims, 4 Drawing Sheets

U.S. PATENT DOCUMENTS

| | | | |
|---|---|---|---|
| 6,556,653 B2* | 4/2003 | Hussein | 378/90 |
| 6,567,496 B1* | 5/2003 | Sychev | 378/57 |
| 6,937,692 B2 | 8/2005 | Johnson et al. | |
| 7,023,957 B2 | 4/2006 | Bijjani et al. | |
| 7,092,485 B2 | 8/2006 | Kravis | |
| 7,103,137 B2* | 9/2006 | Seppi et al. | 378/9 |
| 7,130,371 B2* | 10/2006 | Elyan et al. | 378/57 |
| 7,162,005 B2 | 1/2007 | Bjorkholm | |
| 7,162,007 B2 | 1/2007 | Elyan et al. | |
| 7,190,757 B2 | 3/2007 | Ying et al. | |
| 7,336,767 B1* | 2/2008 | Le | 378/147 |
| 7,356,115 B2* | 4/2008 | Ford et al. | 378/57 |
| 7,356,118 B2 | 4/2008 | Might et al. | |
| 7,366,282 B2* | 4/2008 | Peschmann | 378/57 |
| 7,491,958 B2* | 2/2009 | Zavadtsev et al. | 250/559.4 |
| 7,545,907 B2* | 6/2009 | Stewart et al. | 378/37 |
| 7,856,081 B2* | 12/2010 | Peschmann | 378/57 |
| 2001/0033636 A1 | 10/2001 | Hartick et al. | |
| 2004/0247075 A1 | 12/2004 | Johnson et al. | |
| 2005/0002550 A1 | 1/2005 | Jabri et al. | |
| 2005/0025280 A1 | 2/2005 | Schulte | |
| 2005/0031075 A1 | 2/2005 | Hopkins et al. | |
| 2005/0058242 A1 | 3/2005 | Peschmann | |
| 2005/0111619 A1 | 5/2005 | Bijjani et al. | |
| 2005/0180542 A1 | 8/2005 | Leue et al. | |
| 2005/0256820 A1 | 11/2005 | Dugan et al. | |
| 2006/0098773 A1* | 5/2006 | Peschmann | 378/57 |
| 2006/0204107 A1 | 9/2006 | Dugan et al. | |
| 2006/0233302 A1 | 10/2006 | Might et al. | |
| 2006/0256914 A1 | 11/2006 | Might et al. | |
| 2006/0269114 A1 | 11/2006 | Metz | |
| 2007/0009084 A1 | 1/2007 | Bhatt et al. | |
| 2007/0242797 A1* | 10/2007 | Stewart et al. | 378/16 |
| 2007/0248212 A1 | 10/2007 | Might et al. | |
| 2009/0003651 A1* | 1/2009 | Dugan et al. | 382/103 |
| 2009/0003699 A1* | 1/2009 | Dugan et al. | 382/173 |
| 2009/0052622 A1* | 2/2009 | Dugan et al. | 378/57 |
| 2009/0052732 A1* | 2/2009 | Dugan et al. | 382/100 |
| 2009/0055344 A1* | 2/2009 | Dugan et al. | 706/52 |

OTHER PUBLICATIONS

Wanga, L.; Yuanxiang Li; Jianli Ding; Kangshun Li; "Structural X-ray Image Segmentation for Threat Detection by Attribute Relational Graph Matching"; Date: Oct. 13-15, 2005; ICNN&B '05., International conference on vol. 2, pp. 1206-1211.

Naydenov, S.V.; Ryzhikov, V.D.; Smith, C.F.; "Radiographic Spectroscopy of Atomic Composition of Materials: A Multi-Energy Approach"; Date: Oct. 16-22, 2004; Source: Nuclear Science Symposium Conference Record, 2004 IEEE vol. 3, pp. 1556-1558 vol. 3.

L. Qiang, "The Utility of X-ray Dual-Energy Transmission and Scatter Technologies for Illicit Material Detection", Ph.D. Dissertation, Virginia Polytechnic Institute and State University, Blacksburg, VA, Aug. 1999, pp. 1-4.

A. Fainberg, "Explosives Detection for Aviation Security", Science, pp. 1531-1537, vol. 255, Mar. 1992.

L. Grodzins, "Photons in—Photons Out: Non-Destructive Inspection of Containers Using X-ray and Gamma Ray Techniques", in Proceedings of the First International Symposium on Explosive Detection Technology, Siraj M. Khan (Ed.), pp. 201-211, Nov. 13-15, 1991.

S. Ribaric, K. Kis, "Colour-Based Segmentation of Carry-on Baggage Images", Image and Signal Processing and Analysis, 2001. ISPA 2001. Proceedings of the $2^{nd}$ International Symposium, Jun. 19-21, 2001 pp. 339-344.

J. Liang, B.R. Abidi, M.A. Abidi, "Automatic X-ray Image Segmentation for Threat Detection", Computational Intelligence and Multimedia Applications, 2003. ICCIMA 2003. Proceedings. Fifth International Conference, Sep. 27-30, 2003 pp. 396-401.

M. Sluser, R. Paranjape, "Model-Based Probabilistic Relaxation Segmentation Applied to Threat Detection in Airport X-ray Imagery", Electrical and Computer Engineering, 1999 IEEE Canadian Conference, vol. 2, May 9-12, 1999 pp. 720-726 vol. 2.

S. Wang, J.M. Siskind, "Image Segmentation with Ratio Cut", Pattern Analysis and Machine Intelligence, IEEE Transactions, vol. 25, Issue 6, Jun. 2003 pp. 675-690.

W. Vanzella, V. Torre, "A Versatile Segmentation Procedure", Systems, Man and Cybernetics, Part B, IEEE Transactions, vol. 36, Issue 2, Apr. 2006 pp. 366-378.

V. Mezaris, I. Kompatsiaris, M.G. Strintzis, "A Framework for the Efficient Segmentation of Large-Format-Color Images", Image Processing. 2002. Proceedings. 2002 International Conference, vol. 1, Sep. 22-25, 2002 pp. I-761-I-764 vol. 1.

Y. Shwu-Huey, T. An-Chi W. Chia-Jen, "Segmentation on Color Images Based on Watershed Algorithm", Multimedia Modeling Conference, 2004. Proceedings. $10^{th}$ International Jan. 5-7, 2004 pp. 227-232.

R. Aguilar-Ponce; A. Kumar, J.L. Tecpanecatl-Xihuitl. M. Bayoumi, "An Architecture for Automated Scene Understanding", Computer Architecture for Machine Perception, 2005. CAMP 2005. Proceedings. Seventh International Workshop, Jul. 4-6, 2005 pp. 19-24.

I. Noorzaie, Y.A. Aslandogan, M.E. Celebi, "A System for Distributed Image Acquisition, Content-Analysis and Similarity Retrieval", Information Reuse and Integration, 2004. IRI 2004. Proceedings of the 2004 IEEE International Conference, Nov. 8-10, 2004 pp. 168-173.

B.A. Klock, "Test and Evaluation Report for X-ray Detection of Threats Using Different X-ray Functions", Security Technology, 2005. CCST '05. $39^{th}$ Annual 2005 International Carnahan Conference, Oct. 11-14, 2005 pp. 182-184.

F. Hofer; A. Schwaninger, "Reliable and Valid Measures of Threat Detection Performance in X-ray Screening", Security Technology, 2004. $38^{th}$ Annual 2004 International Carnahan Conference on Oct. 11-14, 2004 pp. 303-308.

R.C. Byrd, J.M. Moss, W.C. Priedhorsky, C.A. Pura, G.W. Richter, K.J. Saeger, W.R. Scarlett, S.C. Scott,; R.L. Wagner, Jr., "Nuclear Detection to Prevent or Defeat Clandestine Nuclear Attack", Sensors Journal, IEEE vol. 5, Issue 4, Aug. 2005 pp. 593-609.

B.R. Abidi, Y. Zheng, A.V. Gribok, M.A. Abidi, "Improving Weapon Detection in Single Energy X-Ray Images Through Pseudocoloring", Systems, Man and Cybernetics, Part C, IEEE Transactions, vol. 36, Issue 6, Nov. 2006 pp. 784-796.

C.R. Jones, R.E. Evans, "Radioisotope Detection and Identification at High Speeds Using Passive Sensors", Aerospace and Electronic Systems magazine, IEEE, vol. 20, Issue 4, Apr. 2005 pp. 3-8.

L. Wang, L. Yuanxiang, J. Ding K. Li, "Structural X-ray Image Segmentation for Threat Detection by Attribute Relational Graph Matching", Neural Networks and Brain, 2005. ICNN&B '05. International Conference, vol. 2, Oct. 13-15, 2005 pp. 1206-1211.

J. H. Graham, Y. Yu, "Computer System Security Threat Evaluation Based Upon Artificial Immunity Model and Fuzzy Logic", Systems, Man and Cybernetics, 2005 IEEE International Conference, vol. 2, Oct. 10-12, 2005 pp. 1297-1302 vol. 2.

E.C. Real, M.J. Kotrlik, M.L. Chevalier, "Adaptive Threat Warning", Signals, Systems and Computers, 2003. Conference Record of the Thirty-Seventh Asilomar Conference, vol. 1, Nov. 9-12, 2003 pp. 812-816 vol. 1.

J. Whiffen, M. Naylor, "Acoustic Signal Processing Techniques for Container Security", Signal Processing Solutions for Homeland Security, 2005. The IEE Seminar on (Ref. No. 2005/11108), Oct. 11, 2005 pp. 13 pp.

B.S. Sharif, S.A. Zaroug, E.G. Chester, J.P. Owen, E.J. Lee, "Bone Edge Detection in Hand Radiographic Images", Engineering in Medicine and Biology Society, 1994. Engineering Advances: New Opportunities for Biomedical Engineers. Proceedings of the $16^{th}$ Annual International Conference of the IEEE, Nov. 3-6, 1994 pp. 514-515 vol. 1.

C. Xi-Ren, L. Ruey-Wen, "General Approach to Blind Source Separation", Signal Processing, IEEE Transactions, see also Acoustics, Speech, and Signal Processing, IEEE Transactions, vol. 44, Issue 3, Mar. 1996 pp. 562-571.

P.S. Mitra, V. Gopalakrishnan, R.L. McNamee, "Segmentation of fMRI Data by Maximization of Region Contrast," Computer Vision and Pattern Recognition Workshop, 2006 Conference, Jun. 17-22, 2006 pp. 88-88.

P.R. Oliveira, R.A.F. Romero, "Enhanced ICA Mixture Model for Image Segmentation", Machine Learning and Applications, 2004. Proceedings. 2004 International Conference, Dec. 16-18, 2004 pp. 288-295.

M. Magadan-Mendez, A. Kivimaki, U. Ruotsalainen, "ICA Separation of Functional Components From Dynamic Cardiac PET Data", Nuclear Science Symposium Conference Record, 2003 IEEE, vol. 4, Oct. 19-25, 2003 pp. 2618-2622, vol. 4.

C. Yen-Wei; Z. Xiang-Yan; L. Hanqing, "Edge Detection and Texture Segmentation Based on Independent Component Analysis", Pattern Recognition, 2002. Proceedings. 16th International Conference, vol. 3, Aug. 11-15, 2002 pp. 351-354 vol. 3.

K. Yanai, K. Deguchi, "An Architecture of Object Recognition System for Various Images Based on Multi-Agent", Pattern Recognition, 1998. Proceedings. Fourteenth International Conference, vol. 1, Aug. 16-20, 1998; pp. 278-281, vol. 1.

M.A. Fouad, A.M. Darwish, F. Bayoumi, S.I. Shaheen, "Model-Based Human Face Detection in Unconstrained Scenes", Image Processing, 2000. Proceedings. 2000 International Conference, vol. 2, Sep. 10-13, 2000 pp. 227-230, vol. 2.

A. Khashman, K.M. Curtis, "Scale Space Analysis and Neural Arbitration for 3-Dimensional Edge Detection", Image Processing and its Applications, 1995, Fifth International Conference, Jul. 4-6, 1995 pp. 183-187.

S. Yih-Ming, W. Jhing-Fa, "Recognition of Handwritten Chinese Postal Address Using Neural Networks", Circuits and Systems, 1998. ISCAS '98. Proceedings of the 1998 IEEE International Symposium, vol. 3, May 31-Jun. 3, 1998 pp. 25-28 vol. 3.

M.A. Ramalho, K.M. Curtis, "Neural Network Arbitration for Edge Detection", Electronics, Circuits, and Systems, 1996. ICECS '96, Proceedings of the Third IEEE International Conference, vol. 2, Oct. 13-16, 1996 pp. 1112-1115 vol. 2.

Chung-Kuo Chang; Huang, J., Video Surveillance for Hazardous Conditions Using Sensor Networks, *Networking, Sensing and Control, 2004 IEEE International Conference*, vol. 2, 2004 pp. 1008-1013 vol. 2.

D. Bona, S., Salvetti, O., An Enhanced Neural System for Biomedical Image Classification, *Image Analysis and Interpretation, 2000. Proceedings. 4th IEEE Southwest Symposium*, Apr. 2-4, 2000 pp. 141-145.

Singh, Sameer, Singh, Maneesha, Review "Explosives Detection Systems (EDS) for Aviation Security", PANN Research, Department of Computer Science, Univ. of Exeter, Devon, UK, 2002 Elsevier Science B.V.; Received Jan. 21, 2002, received in revised form Jun. 3, 2002, www.ComputerScienceWeb.com; Signal Processing 83 (2003), pp. 31-55.

Notice of Allowance dated Jul. 17, 2009, U.S. Appl. No. 12/29,439.

\* cited by examiner

MATERIAL CONTEXT ANALYSIS

The present application claims the benefit of U.S. Provisional Patent Application No. 60/940,632, entitled "Threat Detection System", filed May 29, 2007, which is incorporated herein by reference in its entirety.

Embodiments of the present invention relate generally to automatic analysis of image data and, more particularly, to systems, methods and computer program products for automatic analysis of radiographic image data using material context information.

In performing an analysis of radiographic images to determine whether a potential threat material is present in the image, a need for sensitivity is often balanced against a need for a low false alarm rate. These competing needs are often expressed as requirements that an automatic image analysis system have a certain probability of detection of a potential threat material and a certain confidence of a true positive indication.

Embodiments of the material context analysis (MCA) method and system of the present invention may provide a reduced false alarm rate by increasing both the rate of identifying potential threats and the rate of identifying typical false alarms. The MCA can use a knowledge base including expert knowledge, historical data, or both to provide contextual information for the automatic analysis of estimated materials in a radiographic image.

One exemplary embodiment is a system for contextual analysis of radiographic images of a cargo container. The system can include a processor and a memory for storing instructions that when executed cause the processor to perform a series of steps. The series of steps can include receiving one or more radiographic images of the cargo container, each of the radiographic images can be generated using a different imaging parameter. The system then performs a region analysis including identifying any regions within the radiographic images having a high atomic number, the regions being categorized as being in one of an expected area or a possible threat area. Also, a material feature analysis is performed including identifying features present in the radiographic images that correspond to possible shielding or other context related features. A context information knowledge base is provided and is used to generate, as output from the system, a scene hypothesis using a set of rules, the scene hypothesis being based on the region analysis, the material feature analysis, and the context information knowledge base, and indicating regions within the radiographic images that may contain a threat.

Another exemplary embodiment includes a computer program product for contextual analysis of radiographic images. The computer program product includes a computer readable medium encoded with software instructions that, when executed by a computer, cause the computer to perform a series of steps. The steps include receiving one or more radiographic images and performing a region analysis including identifying any regions within the radiographic images having a high atomic number, the regions being categorized as being in one of an expected non-penetrable area or a possible threat area. The steps also include performing a material feature analysis including identifying features present in the radiographic images that correspond to possible shielding or other context related situations. A context information knowledge base is provided and used to generate, as output, a scene hypothesis using a set of rules, the scene hypothesis being based on the region analysis, the material feature analysis, and the context information knowledge base.

Another embodiment includes a method for analyzing radiographic image data. The method includes receiving a radiographic image and performing a region analysis including identifying a region within the radiographic images having an estimated atomic number within a predetermined range and determining if the region is in an expected location. A material feature analysis is performed to identify whether a feature present in the radiographic image is associated with an obscuration characteristic. Context information is provided and used for generating, as output, a region of interest in the radiographic image, the region of interest being determined based upon a set of rules and the region analysis, the material feature analysis, and the context information.

BRIEF DESCRIPTION

DETAILED DESCRIPTION

In general, the MCA assists in an automatic image analysis system, such as a nuclear threat detection system, by providing an automatic analysis of the environment, or context, surrounding an object or region of interest (ROI) identified in an image. The MCA can be embodied as a rule based processor which looks for suspicious areas and locations of an image. For example, the MCA can look for materials occurring in places where they typically do not occur in a certain type of image. Also, the MCA can identify mixtures of materials that look suspicious. Basically, the threat levels of objects are analyzed within the context of a scene and a result of this analysis can be used to influence the confidence value for triggering an alert or indication of a potential threat. By incorporating context analysis, a false alarm rate can be decreased.

An example of a potential threat is a high-Z (or high atomic number) material located in an image or in a suspicious location within the image. Elements or materials with a high atomic number (e.g., atomic number >72) include Special Nuclear Materials (SNM) such as plutonium and highly enriched uranium, as well as some elements or materials that can be used to shield SNM or other radioactive materials from passive gamma radiation detection. It is desirable to be able to automatically detect SNM in a cargo conveyance (e.g., shipping container), that can include the container, a trailer, and a truck. In an embodiment, the present invention can be used to automatically detect material suspected of having a high atomic number as well as materials that may be used to shield SNM. Also, an embodiment can include a capability for detecting traditional contraband (e.g., weapons or drugs) using an approach that is automatic or manual or both.

Figure 1:
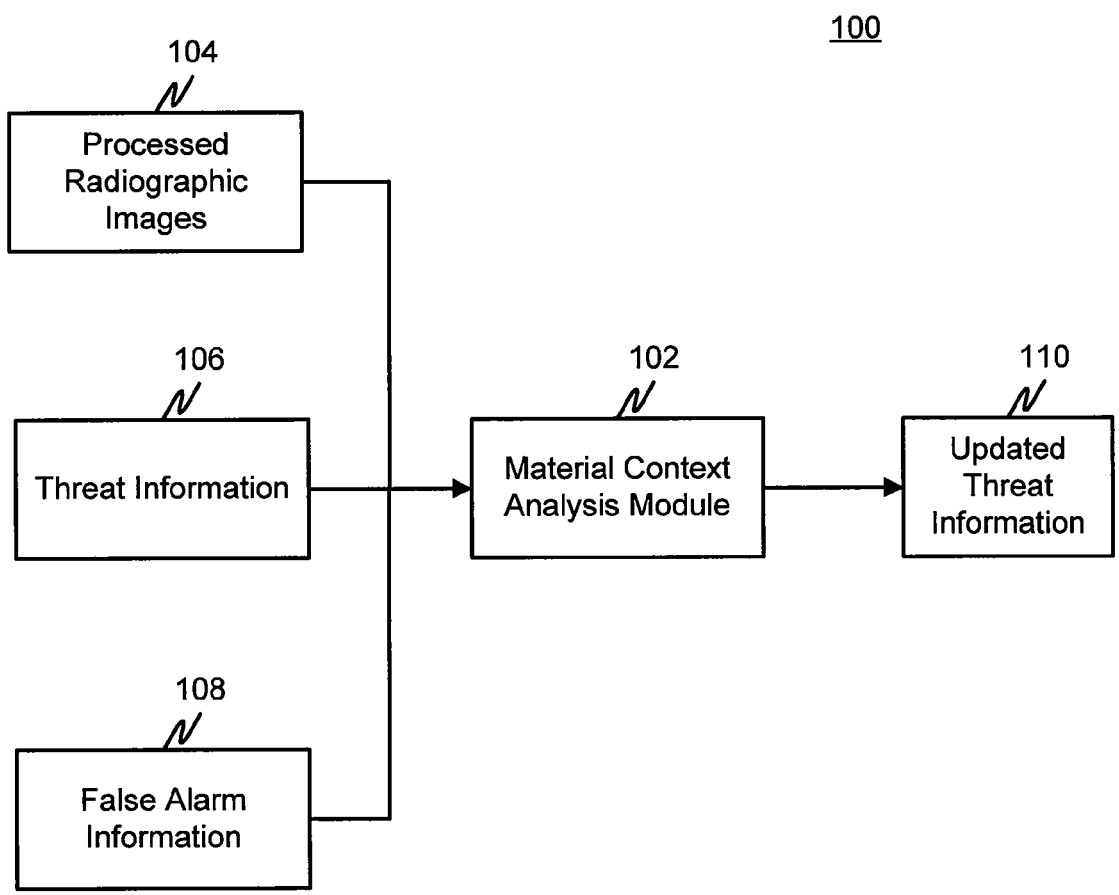
FIG. 1 is a block diagram of an exemplary material context analysis module.

FIG. 1 shows an exemplary embodiment of a system for material context analysis of radiographic images. The system 100 includes a material context analysis (MCA) module 102. The MCA module 102 receives input in the form of processed radiographic images 104, suspected or estimated threat information 106, and false alarm information 108. The MCA module provides, as output, updated threat information 110.

The processed radiographic images 104 can include gray scale or color images of the object being scanned (e.g., a cargo container). The images can be based on raw radiographic data or material atomic number estimates that correspond to at least a portion of the image, or both. The images may be combined such that a gray scale image contains the raw radiographic data and the estimated atomic number for the materials within the image. Each of the radiographic images may be generated using a different imaging characteristic, such as x-ray energy level. The radiographic images 104 can also include a Z-value map containing estimated atomic numbers corresponding to a pixel or region of one or more of the images.

The suspected (or estimated) threat information 106 can be provided by another module within a nuclear detection system or from an external module or system. The threat information 106 can include one or more regions of interest within an image. The threat information 106 can also include a confidence value for each region of interest as well as other information, such as suspected material type.

The false alarm information 108 can include information about typical false alarms regions of an image. For example, it may be the case that a particular portion of an image typically contains a high-Z material (such as the lead within a vehicle battery) and that high-Z material in these locations (e.g., the front of the vehicle in the engine compartment) is not to be identified as suspicious. The false alarm information can include information about false alarm areas (e.g. areas that typically produce false alarms) that are known in advance and which can be supplied to the MCA module 102 in order to help reduce the false alarm rate.

In operation, the MCA module 102 takes the radiographic images 104, the threat information 106, and false alarm information 108 and processes these inputs using rules or equations that either confirm that a suspected threat is present or dispel a suspected threat as being a false alarm. The confirming or dispelling can be in the form of increasing or decreasing a confidence level that a suspected region of interest is an actual threat. An example of a rule is that a high-Z material within a region of otherwise low-Z material may be identified as a suspected threat. This type of material placement may indicate an attempt to hide a high-Z material (such as SNM) within a quantity of low-Z material (such as grain). In general, the particular rules or equations can be developed based on the types of material being scanned and the types of threats being looked for. The rules and equations can also represent the knowledge and experience of the security personnel familiar with the type of search being carried out.

Once the images have been processed by the MCA module 102, the updated threat information 110 is output in the form of computer readable data or human readable information or both. In an example of human readable information, the updated threat information can include a scene hypothesis having a modified form of a container image; the modified form includes potential threat symbology indicating regions within the radiographic images that may contain a threat. The scene hypothesis can further include false alarm symbology indicating regions having a high estimated Z-value and being identified by the system as false alarms, the false alarm symbology would typically be different from the potential threat symbology so that an operator can be informed of the threat/false alarm determination of the system. For example, potential threat areas could be shaded red (or surrounded by a red outline) and false alarm areas could be shaded yellow (or surrounded by a yellow outline). In general, any symbology could be used to indicate threat and false alarm information including alphanumeric or graphical or both.

Figure 2:
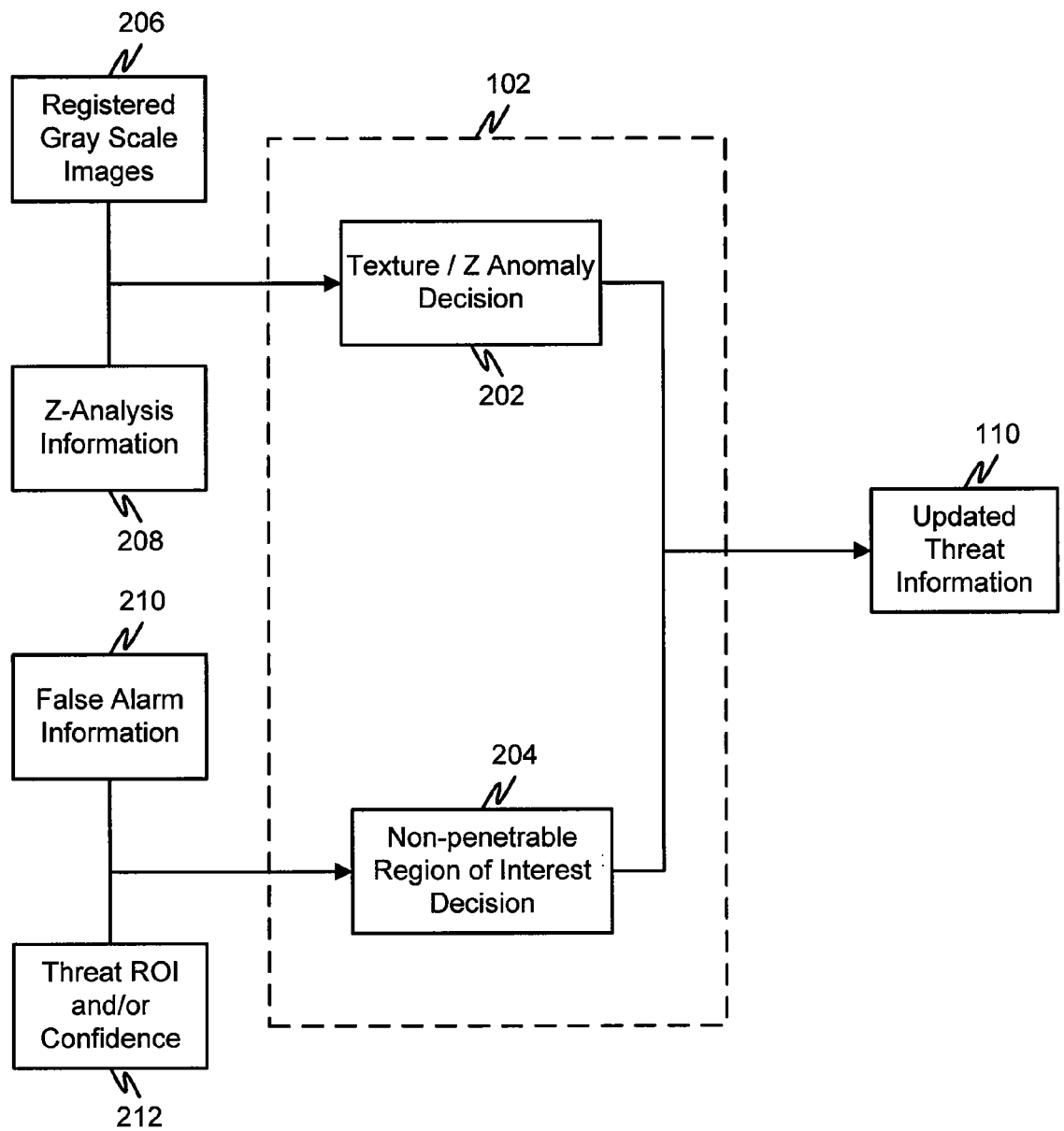
FIG. 2 is a block diagram of an exemplary material context analysis module showing the inputs and internal processing routines.

FIG. 2 is a block diagram of an exemplary material context analysis module showing the inputs and internal processing routines. In particular, the MCA module 102 includes modules for texture/Z-anomaly decisions 202 and non-penetrable regions of interest decisions 204. The texture/Z-anomaly decision module 202 receives registered gray scale images 206 and Z-analysis information 208 as input. The non-penetrable regions of interest decision module 204 receives false alarm information 210 and threat ROI/confidence information 212 and can also access the registered gray scale images 206 and the Z-analysis information 208. The MCA module 102 outputs updated threat information 110 as described above.

In operation, the texture/Z-anomaly decision module 202 analyzes the gray scale images 206 and the Z-analysis information 208 to determine if any anomalies are present, such as a high-Z material within an area of low-Z material. This can be accomplished in a simple form by evaluating the line or edge boundaries in an image and the material Z-values associated with the materials on each side of an edge or boundary. In more complex situations, a region-based approach can be used, such as connected region analysis or other suitable region-based segmenting method.

The non-penetrable regions of interest decision module 204 analyzes the registered gray scale images 206 and the Z-analysis information 208 in view of the false alarm information 210 and the threat ROI/confidence information 212 in order to identify any high-Z areas that are known to be typical false alarm areas and mark those. Also, the non-penetrable regions of interest decision module 204 determines if any high-Z regions are present in the images that are not associated with typical false alarms and marks those regions as potential threats. In other words, any regions containing high-Z material that are not known false alarm regions are marked as potential or suspected threats. The analysis performed by the non-penetrable regions of interest decision module 204 can also take into account the confidence of the various threat or ROIs that have been previously identified.

The non-penetrable regions of interest decision module 204 can also generate a map of the radiographic image that includes areas where shielding materials may be present. The map of potential shielding can be compared to the areas of suspected threats to further help identify possible threats.

The outputs of the texture/Z-anomaly decision module 202 and the non-penetrable regions of interest decision module 204 are combined to update the threat information and provide the updated threat information 110 as output from the MCA module 102. An example of computer readable output data includes a copy of the threat ROI/confidence data 212 that has been updated by the MCA module 102 to include modified ROIs/confidences, if applicable.

Figure 3:
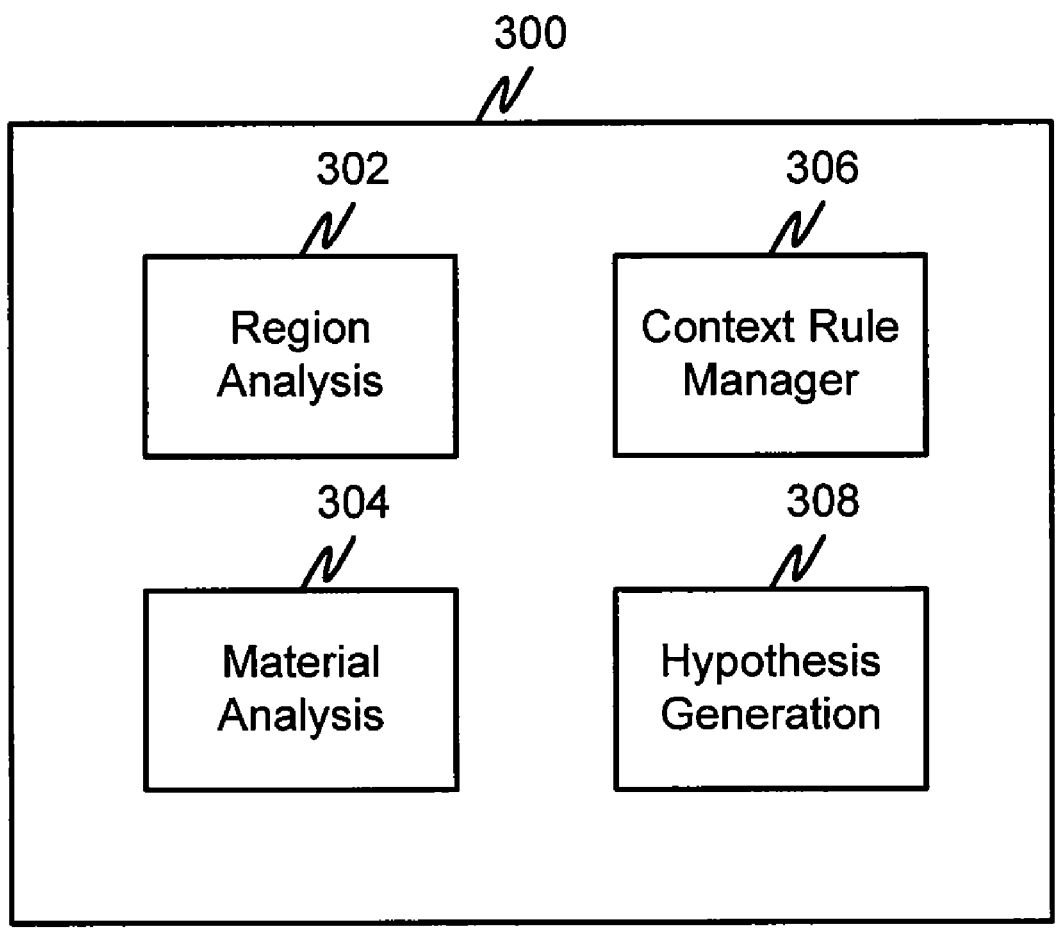
FIG. 3 is a block diagram of an exemplary material context analysis module showing four sub-modules.

FIG. 3 is a block diagram of an exemplary material context analysis module showing four sub-modules. In particular, the material context analysis (MCA) module 300 includes sub-modules for region analysis 302, material analysis 304, context rule management 306, and hypothesis generation 308.

Region analysis includes applying container or cargo configuration data (e.g., such as a shipping manifest) in order to evaluate areas of a scene (e.g., an image of a cargo container). The two primary areas of identification are threat areas and false alarm areas. The region analysis sub-module 302 can include using known false alarm areas and areas of the images containing material estimated to have a high Z-value in a manner similar to that mentioned above in relation to the non-penetrable region of interest module 204.

Material analysis includes using the Z-value information for the various objects in a surveillance area to identify texture anomalies and suspected shielding. The material analysis sub-module 304 can perform the material analysis in a manner similar to that described above in relation to the texture/Z-anomaly decision module 202.

The context rule management module 306 includes the logic and data for storing and providing context rules for use by an MCA module. The context rules can have two parts: a physical characteristic part that can include one or more factors such as cross-sectional area, dimensions, Z-value, or the like; and a context part that can be used to help determine if the material is out of context and, therefore, a potential threat.

The hypothesis generation module 308 generates hypotheses regarding the presence of potential threats and false alarms areas in radiograph images. Generating a hypothesis can include pattern assessment (e.g., type of pattern in image data), boundary analysis (e.g., objects adjacent to the pattern), and data association (e.g., the pattern's location within the image). The hypothesis generation module can use expert knowledge (or rules) on where various types of materials should be located within a container, for example, in conjunction with a basic physical description or characteristic of an object (e.g., cross-sectional area, Z-value, or the like).

An MCA module could function fully automatically or in a semi-automatic mode that includes a degree of manual intervention or augmentation. For example, the material context analysis process could include an iterative process by which an operator works in conjunction with the MCA module to identify threat areas and false alarm areas. The operator could confirm threats or false alarms. Also, the operator could suggest areas for automatic analysis.

Figure 4:
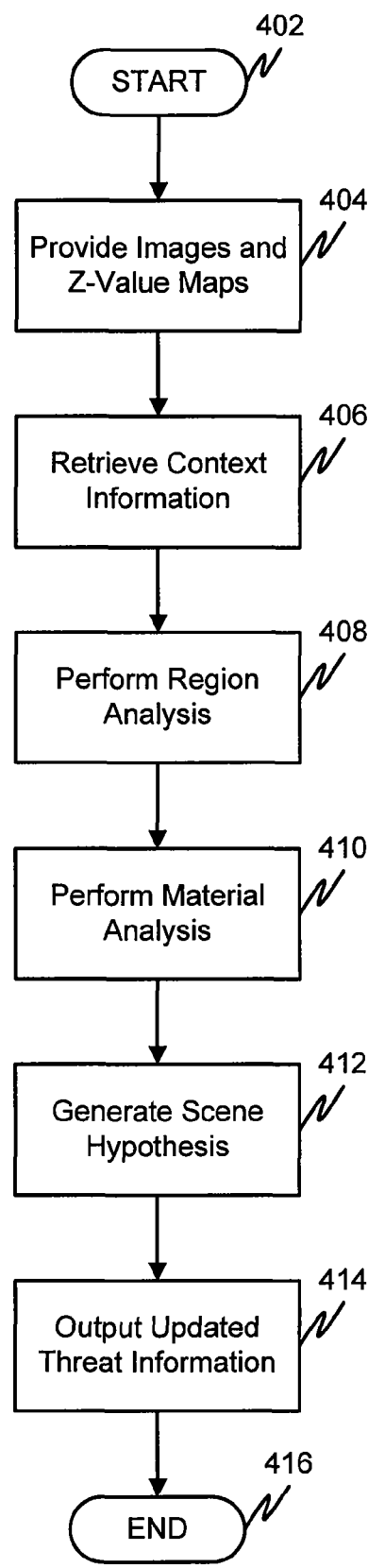
FIG. 4 is a flowchart of an exemplary method for material context analysis.

FIG. 4 is a flowchart of an exemplary method for material context analysis. The steps shown in the method of FIG. 4 largely correspond to the functions of the sub-modules described above in relation to FIG. 3. It will be appreciated that the steps in FIG. 4 can be performed sequentially or in parallel or a combination of the two.

In FIG. 4, the method begins at step 402 and continues to step 404. In step 404, one or more gray scale images and associated Z-value maps are provided. The gray scale images could be registered in cases where more than one image is provided. Also, threat information may be provided along with the images and Z-value maps. The threat information can include ROI and confidence values. The method continues to step 406.

In step 406, context rules (or information) are retrieved. The context rules may be retrieved from a local memory or may be provided from an external source. The method continues to step 408.

In step 408, region analysis is performed. The region analysis is discussed above in relation to the region analysis sub-module 302. The method continues to step 410.

In step 410, material analysis is performed. The material analysis is discussed above in relation to the material analysis sub-module 304. The method continues to step 412.

In step 412, a scene hypothesis is generated. The scene hypothesis can include a modified form of a portion of an input image as discussed above. The method continues to step 414.

In step 414, updated threat information is output. The updated threat information can include the scene hypothesis. Alternatively, the updated threat information can be based on the scene hypothesis. Also, as discussed above, the output can be in a form that is human-readable, machine-readable, or both. The method continues to step 416 where the method ends.

It will be appreciated that steps 404-414 may be repeated in whole or in part in order to accomplish a contemplated material context analysis task. Further, it should be appreciated that the steps mentioned above may be performed on a single or distributed processor. Also, the processes, modules, and sub-modules described in the various figures of the embodiments above may be distributed across multiple computers or systems or may be co-located in a single processor or system.

Embodiments of the method, system, and computer program product for material context analysis, may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a PLD, PLA, FPGA, PAL, or the like. In general, any process capable of implementing the functions or steps described herein can be used to implement embodiments of the method, system, or computer program product for material context analysis.

Furthermore, embodiments of the disclosed method, system, and computer program product for material context analysis may be readily implemented, fully or partially, in software using, for example, object or object-oriented software development environments that provide portable source code that can be used on a variety of computer platforms. Alternatively, embodiments of the disclosed method, system, and computer program product for material context analysis can be implemented partially or fully in hardware using, for example, standard logic circuits or a VLSI design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product for material context analysis can be implemented in hardware and/or software using any known or later developed systems or structures, devices and/or software by those of ordinary skill in the applicable art from the function description provided herein and with a general basic knowledge of the computer, radiographic, and scene analysis arts.

Moreover, embodiments of the disclosed method, system, and computer program product for material context analysis can be implemented in software executed on a programmed general purpose computer, a special purpose computer, a microprocessor, or the like. Also, the method for material context analysis of this invention can be implemented as a program embedded on a personal computer such as a JAVA® or CGI script, as a resource residing on a server or image processing workstation, as a routine embedded in a dedicated processing system, or the like. The method and system can also be implemented by physically incorporating the method for material context analysis into a software and/or hardware system, such as the hardware and software systems of multi-energy radiographic inspection systems.

It is, therefore, apparent that there is provided, in accordance with the present invention, a method, computer system, and computer program product for material context analysis. While this invention has been described in conjunction with a number of embodiments, it is evident that many alternatives, modifications and variations would be or are apparent to those of ordinary skill in the applicable arts. Accordingly, Applicant intends to embrace all such alternatives, modifications, equivalents and variations that are within the spirit and scope of this invention.

What is claimed is:

1. A system for contextual analysis of radiographic images of a cargo container, the system comprising:

a material context analysis computer module including software instructions stored on a non-transitory computer readable medium, the software instructions, when executed, cause the material context analysis module to perform steps comprising:

receiving one or more radiographic images of the cargo container, each radiographic image generated using a different imaging parameter;

performing a region analysis including identifying any regions within the radiographic images having a high atomic number, the regions being categorized as being in one of an expected area or an area associated with a potential threat;

performing a material feature analysis including identifying features present in the radiographic images that correspond to possible shielding;

receiving data from a context information knowledge base; and generating, as output from the computer module, a scene hypothesis using a set of rules, the scene hypothesis being based on the region analysis, the material feature analysis, and the data received from the context information knowledge base, the scene hypothesis indicating regions within the radiographic images that may contain a threat.

2. The system of claim 1, wherein the radiographic images include a gray scale image and a map of estimated material Z-values.

3. The system of claim 1, wherein the context information knowledge base includes information about expected high Z-value regions of radiographic images.

4. The system of claim 1, wherein the different imaging parameter includes a different energy level used for generating radiographic images.

5. The system of claim 1, wherein each radiographic image is taken at a different energy level.

6. The system of claim 1, wherein the scene hypothesis includes a modified form of a container image, the modified form including potential threat symbology indicating regions within the radiographic images that may contain a threat.

7. The system of claim 1, wherein the scene hypothesis further includes false alarm symbology indicating regions having a high estimated Z-value and being identified by the system as false alarms, the false alarm symbology being different from the potential threat symbology.

8. A computer program product for contextual analysis of radiographic images, the computer program product comprising:

a non-transitory computer readable medium encoded with software instructions that, when executed by a computer, cause the computer to perform the steps of:

receiving one or more radiographic images;

performing a region analysis including identifying any regions within the radiographic images having a high atomic number, the regions being categorized as being in one of an expected non-penetrable area or a possible threat area;

performing a material feature analysis including identifying features present in the radiographic images that correspond to possible shielding;

providing a context information knowledge base; and generating, as output, a scene hypothesis using a set of rules, the scene hypothesis being based on the region analysis, the material feature analysis, and the context information knowledge base.

9. The computer program product of claim 8, wherein the radiographic images are images of a cargo container.

10. The computer program product of claim 8, wherein each radiographic image is generated using a different imaging parameter.

11. The computer program product of claim 8, wherein the different imaging parameter includes a different radiographic energy level.

12. The computer program product of claim 8, wherein the scene hypothesis includes a modified form of a container image, the modified form including potential threat symbology indicating regions within the radiographic images that may contain a threat.

13. The computer program product of claim 8, wherein the scene hypothesis further includes false alarm symbology indicating regions having a high estimated Z-value and being identified by the system as false alarms, the false alarm symbology being different from the potential threat symbology.

14. A method for analyzing radiographic image data, the method comprising:

using a processor to perform the steps of:

receiving a radiographic image;

providing context information;

performing a region analysis including identifying a region within the radiographic images having an estimated atomic number within a predetermined range and determining if the region is in an expected location using the context information;

performing a material feature analysis to identify whether a feature present in the radiographic image is associated with an obscuration characteristic; and generating, as output, a region of interest in the radiographic image, the region of interest being determined electronically based upon a set of rules and the region analysis, the material feature analysis, and the context information.

15. The method of claim 14, wherein the radiographic image is an image of a cargo container.

16. The method of claim 14, wherein the region of interest includes a modified form of a portion of the radiographic image, the modified form including potential threat symbology indicating a region within the radiographic image that may contain a threat.

17. The method of claim 14, wherein the region of interest further includes false alarm symbology indicating a region having a high estimated Z-value and being identified by the system as a false alarm, the false alarm symbology being different from the potential threat symbology.

18. The method of claim 14, wherein the obscuration characteristic is a very high-Z material adjacent to a high-Z material so as to shield the high-Z material.

19. The method of claim 14, wherein the region analysis includes using known false alarm areas associated with the cargo container.

20. The method of claim 14, wherein the context information includes a physical feature of a material and context information.

* * * * *